United States Patent

Horrobin et al.

[11] Patent Number: 5,888,541
[45] Date of Patent: Mar. 30, 1999

[54] FATTY ACID TREATMENT

[75] Inventors: David F. Horrobin; Brenda E. Reynolds, both of Guildford, England

[73] Assignee: Scotia Holdings PLC, United Kingdom

[21] Appl. No.: 784,105

[22] Filed: Jan. 15, 1997

Related U.S. Application Data

[62] Division of Ser. No. 106,989, Aug. 16, 1993, Pat. No. 5,618,558.

[30] Foreign Application Priority Data

Aug. 21, 1992 [GB] United Kingdom .................. 9217781

[51] Int. Cl.$^6$ ............................... A61K 35/78; A61K 9/20
[52] U.S. Cl. ...................... 424/464; 424/195.1; 424/451; 424/489; 514/560
[58] Field of Search ..................................... 424/464, 451, 424/489, 195.1; 514/560

[56] References Cited

U.S. PATENT DOCUMENTS 4,855,136  8/1989  Horrobin et al. ...................... 424/602

FOREIGN PATENT DOCUMENTS 0 261 814 A2  3/1988  European Pat. Off. .
0 517 425 A1  12/1992  European Pat. Off. .
1 417 119  12/1975  United Kingdom .

OTHER PUBLICATIONS

Derwent Abstract of Japanese 89–233158 (published JP 1 157912 Jun. 21, 1989.

Pathologie Biologie 24, No. 3, 212–225 (1976).

*Primary Examiner*—Thurman K. Page
*Assistant Examiner*—James M. Spear
*Attorney, Agent, or Firm*—Nixon & Vanderhye

[57] ABSTRACT

Increase gut calcium absorption in humans or animals by the administration of GLA, DGLA or LA as such or in salt or other pharmacologically acceptable form, optionally in association with EPA, DHA or other EFA in similar forms, specifically useful in the treatment of osteoporosis.

11 Claims, No Drawings

FATTY ACID TREATMENT

This application is a Division of Ser. No. 08/106,989 filed Aug. 16, 1993 now U.S. Pat. No. 5,618,558

FIELD OF INVENTION

This invention relates to fatty acid treatments, and in particular to enhancing absorption of calcium from the gut, and more particularly to treatment of osteoporosis.

FATTY ACIDS

The pathways of conversion of the main series of polyunsaturated fatty acids in the body are as in Table 1 below:

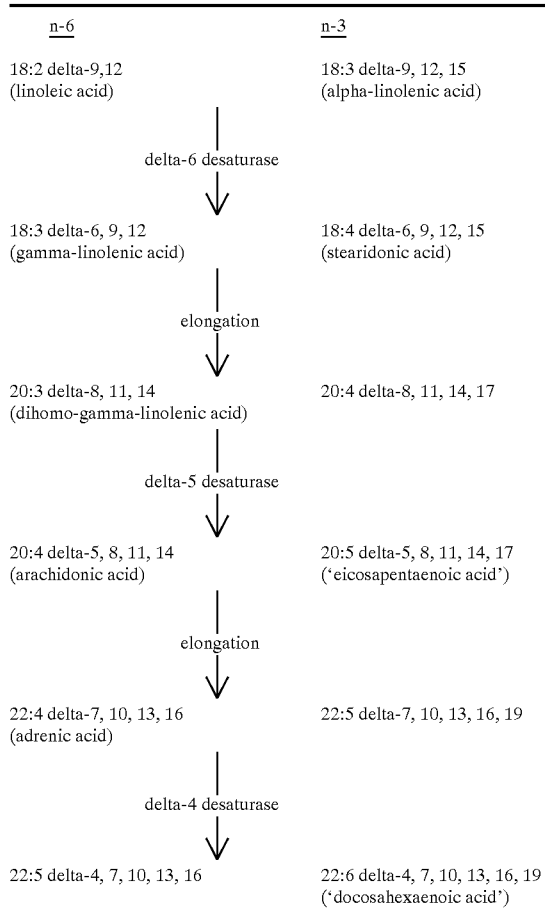

TABLE 1

The above pathways are not normally reversible nor, in man, are n-3 and n-6 series acids interconvertible.

The acids, which in nature are of the all-cis configuration, are systematically named as derivatives of the corresponding octadecanoic, eicosanoic or docosanoic acids, e.g. delta-9, 12-octadecadienoic acid or delta-4,7,10,13,16,19 docosahexaenoic acid, but numerical designations such as, correspondingly, 18:2 n-6 or 22:6 n-3 are convenient. Initials, for example. EPA for the 20:5 n-3 acid (eicosapentaenoic acid) or DHA for the 22:6 n-3 acid (docosahexaenoic acid), are also used but do not serve when n-3 and n-6 acids of the same chain length and degree of unsaturation exist as for example with the 22:5 acids. Trivial names in more or less common use in the n-6 series are as shown. Of the n-3 series only 18:3 n-3 has a commonly used trivial name, alpha-linolenic acid, though the name stearidonic acid is coming into use for the 18:4 n-3 acid and the names eicosapentaenoic acid and docosahexanenoic acid as such are also used. The alpha isomer of linolenic acid was characterised earlier than gamma-linolenic acid and reference in the literature simply to linolenic acid, especially in the earlier literature, is to the alpha-acid.

CALCIUM ABSORPTION, DISCUSSION AND EXPERIMENTAL

Efficient absorption of calcium in humans and animals is significant for at least two reasons:
1. Low calcium absorption coupled with normal or excessive urine calcium excretion can lead to a negative calcium balance.
2. Calcium is required for normal bone strength, and inadequate gut calcium absorption can contribute to weakening of the bones and the development of osteoporosis, a major medical problem.

We have previously discovered a new and safe way of reducing calcium excretion by the administration of gamma-linolenic acid (GLA), or GLA in combination with eicosapentaenoic acid (EPA), the subject of EP-A1-0,517,425. As discussed above, GLA is the first metabolite of linoleic acid, the major essential fatty acid in the diet. Linoleic acid is converted to GLA by the enzyme delta-6-desaturase. However, this step is slow and rate limiting even in the normal body and as a result there are advantages in the administration of GLA directly.

Studies conducted in animals and in man showed that the optimal effect on reducing urine calcium excretion was achieved using a combination of GLA and EPA, although both fatty acids individually also elicited a response.

Because of this, a further human clinical study was conducted in 30 recurrent, hypercalcuric stone formers. On entry into the trial all patients were taken off any previous treatment and stabilised on a standard calcium diet (800 mg calcium per day) which was maintained for the study period. After 14 days on the standard calcium diet, patients were allocated to one of 3 groups and given the following treatment for 12 weeks.

Group 1 6 g cold water marine fish oil (FO) per day (300 mg EPA);

Group 2 6 g evening primrose oil (EPO) per day (540 mg GLA);

Group 3 6 g of an 80:20 combination of EPO and FO (475 mg GLA, 238 mg EPA).

At the end of the 14 day stabilisation period a baseline $Ca^{45}$ absorption test was conducted and this was repeated after 12 weeks of treatment as above. The $Ca^{45}$ absorption test results are summarised below:

| Treatment | Baseline | 12 weeks |
|---|---|---|
| FO | 0.36 ± 0.04 | 0.44 ± 0.06 |
| EPO | 0.38 ± 0.03 | 0.55 ± 0.07 |
| EPO/FO | 0.43 ± 0.07 | 0.68 ± 0.11 |

There was a significant increase in fractional $Ca^{45}$ absorption in both the EPO and EPO/FO treated patients although the latter were higher.

THE INVENTION

Based on the above, the invention in one aspect lies in the use of GLA and/or its immediate and rapidly produced metabolite DGLA, in the preparation of a medicament for, or in a method of, securing increase of gut calcium absorption. Because linoleic acid (LA) is a precursor of GLA it has some effect though its conversion is slow. The invention therefore includes the use of linoleic acid, and as noted below has particular reference to osteoporosis or other calcium deficiency disease.

Alternatively, the invention may be regarded as lying in a method of increasing the systemic calcium pool by stimulating both an increased absorption of and a reduction of urinary excretion of calcium, wherein an effective daily amount of GLA or DGLA, or LA, is administered in any convenient form to animals or humans particularly those suffering from or at risk of osteoporosis or other calcium deficiency disease. The invention further includes the use of GLA, DGLA or LA in the preparation of a medicament for such a method.

Equally in the use of GLA and/or DGLA in preparation of medicaments or in treatment as above, the invention may be regarded simply as the treatment or prevention of osteoporosis or other condition defining disease in either animals or humans.

As noted, GLA in the body is very rapidly converted to dihomo-gamma-linolenic acid (DGLA); DGLA therefore has a very similar effect to GLA.

As discussed further below GLA or DGLA may be used in any appropriate form, including but not limited to triglyceride, diglyceride, monoglyceride, free fatty acid, any appropriate ester, any appropriate salt including the lithium, sodium, potassium, calcium, zinc, magnesium or other salt, phospholipid, amide or any other pharmacologically acceptable form.

The preferred dose range is 0.01 to 1,000 mg/kg/day, more preferably 0.5 to 50 mg/kg/day, very preferably 2 to 30 mg/kg/day of GLA or DGLA, and medicaments are readily prepared in dosage unit form to administer such amounts (related to a 70 kg human adult). The calcium salts would be particularly appropriate for the treatment of osteoporosis since they would provide a calcium supplement at the same time as increasing its absorption and reducing excretion.

The GLA or DGLA may be used with any essential fatty acids of the n-6 or n-3 series, including, for example, arachidonic acid, alpha-linolenic acid, eicosapentaenoic acid or docosahexaenoic acid, in like doses. In particular, in view of results on human gut calcium absorption, GLA in combination with EPA and/or its metabolite DHA is desirable, producing particularly advantageous effects.

ROUTES OF ADMINISTRATION

Oral, parenteral (sub-cutaneous, intramuscular, intravenous or by any other appropriate route), enteral, topical in the form of appropriate GLA-containing ointments, creams, lotions, patches, etc. vaginal or rectal are among suitable routes of administration.

DERIVATIVES OF EFAs

As indicated above, the acids may be used as such or as pharmaceutically acceptable and physiologically equivalent derivatives as, for example, detailed herein for GLA and DGLA, and reference to any of the acids is to be taken as including reference to the acids when in the form of such derivatives. Equivalence is demonstrated by entry into the pathway quoted herein, as evidenced by effects corresponding to those of the acids themselves or their natural glyceride esters. Thus, indirect identification of useful derivatives is by their having the valuable effect in the body of the acid itself, but conversion can be shown directly by gas chromatographic analysis of concentrations in blood, body fat, or other tissue by standard techniques, for example those of Pelick et al, page 23, "Analysis of Lipids and Lipoproteins" Ed Perkins, American Oil Chemists Society, Champaign, Ill., U.S.A.

In outline the method is suitably that plasma samples (1 ml) are extracted with chloroform:methanol (2:1). The extract is filtered through sodium sulphate, evaporated to dryness, and taken up in 0.5 ml chloroform:methanol. The lipid fractions are separated by thin layer chromatography or silica gel plates. The phospholipid fraction, taken to reflect essential fatty acid contents most sensitively, is methylated using boron trifluoride-methanol. The resulting methyl esters of the fatty acids are separated and measured using a Hewlett-Packard 5880 gas chromatograph with a six foot column packed with 10% Silar on Chromosorb WAW 106/230. The carrier gas is helium (30 ml/min). Oven temperature is programmed to rise from 164° C. to 190° C. at 2° C./min. Detector temperature is 220° C. and injector temperature 200° C. Retention times and peak areas are automatically computed by Hewlett-Packard Level 4 integrator. Peaks are identified by comparison with standard fatty acid methyl esters.

DIETARY COMPOSITIONS

The invention is chiefly described in terms of methods of treatment and in the use of GLA or DGLA in the preparation of pharmaceutical compositions, but it will be understood that the gamma-linolenic and other EFAs, being in the nature of dietary supplements, can be incorporated in a dietary margarine or other foodstuff and such are to be understood as within the term pharmaceutical composition or medicament herein (including the claims) when for the purposes set out.

If desired, pharmaceutical compositions may be produced for use in the invention by associating the natural or synthetic acids, as such or as derivatives, with an acceptable pharmaceutical vehicle. It is, however, at present convenient to provide at least GLA in the form of an available oil having a high GLA content, hence reference to "oils" herein.

One source of oils currently available is the seed of evening primrose species such as *Oenothera biennis L.* and *Oenothera lamarckiana*, the oil extract therefrom containing about 8% GLA and about 72% linoleic acid in the form of their glycerides, together with other glycerides (percentages based on total fatty acids). Other sources of GLA are borage species such as *Borago officinalis* which provide a richer source than Oenothera oil. Oils from the seeds of members of the Ribes family are also often rich in GLA. Recent studies on fungi which can be cultivated by fermentation promise a fungal oil source. Some algae also produce GLA and may be harvested or cultured. Synthesis is also possible. The oil is extracted from the seed by one of the conventional methods of extraction such as cold pressure, screw pressure after partially cooking the seed, or solvent extraction.

Fractionation of a typical sample of evening primrose oil as used in the work reported herein in the form of methyl esters shows the relative proportions:

| | |
|---|---|
| Palmitate | 6.15 |
| Stearate | 1.6 |
| Oleate | 10.15 |

| | |
|---|---|
| Linoleate | 72.6 |
| Gamma-linolenate | 8.9 |

The seed oil extracts referred to above can be used as such or can, for example, if desired, be fractionated to yield an oily composition containing the triglycerides of gamma-linolenic and linoleic acids as the main fatty acid components, the gamma-linolenic acid content being, if desired, a major proportion. Seed oil extracts appear to have a stabilising effect upon DGLA if present.

SOURCES OF OTHER ACIDS

DGLA can be prepared by chemical synthesis or by fungal or algal fermentation. For the higher n-6 acids, natural sources of 22:4 and 22:5 n-6 acids include adrenal glands (22:5) and kidneys (22:4) obtained from slaughter houses, which also give AA sources.

The n-3 acids have long been available from marine oils, particularly the 20:5 n-3 (EPA) and 22:6 n-3 (DHA) acids, and more recently from microbial and algal fermentation. They can be isolated from these sources by, for example, saponification under mild non-oxidising conditions followed by preparative gas liquid chromatography. Synthesis is difficult but not impossible and provides another source.

PHARMACEUTICAL PRESENTATION

As mentioned briefly above, the compositions are conveniently in a form suitable for oral, topical, parenteral or other route of administration in a suitable pharmaceutical vehicle, well known generally for any particular kind of preparation. Thus, for example, tablets, capsules, ingestible liquid or powder preparations can be prepared as required, and topical preparations also when the gamma-linolenic acid or other acids are absorbed through the skin. Injectable solutions of hydrolysed Oenothera or other oil may be prepared using albumin to solubilise the free acid. Emulsions and salts can also be administered by infusion or injection.

Advantageously, a preservative is incorporated into the preparation. Alpha-tocopherol in a concentration of about 0.1% by weight has been found suitable for the purpose and is one of a number of possible stabilisers well known in the field and including also for example ascorbyl palmitate and stearate.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

The composition may also be in the form of whips, emulsions, suspensions, pessaries, suppositories, transdermal devices or any other appropriate forms.

EXAMPLES

The following are examples of compositions and their administration for the purposes discussed herein.

1. Administration of 100 mg to 2,000 mg of GLA per day in the form of soft or hard gelatin capsules or tablets providing:
   a. 40 to 80 mg per capsule of GLA in the form of evening primrose oil.
   b. 50–150 mg per capsule of GLA in the form of borage, blackcurrant, fungal or other appropriate oil.
   c. 100–150 mg GLA per capsule in the form of triglyceride GLA, or any appropriate salt of GLA, such as the lithium or calcium or magnesium or zinc or potassium salts.

2. Administration of DGLA in a dose of 100 mg to 2,000 mg per day in the forms of 1c above.

3. Administration of GLA or DGLA in association with EPA, with or without DHA, for example as 40 to 80 mg GLA per capsule in the form of evening primrose oil together with 10 mg to 100 mg per capsule of EPA in the form of cold water marine fish oil.

4. Administration of GLA or DGLA in the form of a soluble powder or effervescent granule formed from any appropriate salt of GLA as in 1c above and excipients such as citric acid monohydrate, sodium bicarbonate or other dibasic acids such as tartaric or maleic acid plus sweeteners such as sucrose or sorbitol and flavourings.

5. Administration of GLA or DGLA in the form of liquid evening primrose, borage or other appropriate oil as the oil itself or as a whip or emulsion prepared with appropriate flavours and stabilisers.

6. Administration of GLA or DGLA in any appropriate chemical form, microencapsulated using starch, gelatin, gum arabic or other appropriate formulation.

7. Administration of GLA in the form of pessaries, suppositories, skin patches or any other appropriate route.

8. Calcium-GLA tablets or soft or hard gelatin capsules containing 500 mg of calcium-GLA salt to be taken 1–5 times/day.

We claim:

1. A method for treating humans or animals having inadequate gut calcium absorption thereby increasing gut calcium absorption in humans or animals, said method comprising administering to said humans or animals gamma-linolenic acid (GLA) or dihomo-gamma-linolenic acid (DGLA) as such or in salt form other than the calcium salt or in other pharmacologically acceptable form convertible thereto in the body, optionally in association with eicosapentaenoic acid (EPA), docosahexaenoic acid (DHA) or other essential fatty acid of the n-3 or n-6 series additional to the GLA or DGLA as such or in salt or other pharmacologically acceptable form convertible thereto in the body.

2. A method for increasing the systemic calcium pool by stimulating both an increased absorption of and a reduction of urinary excretion of calcium in humans or animals, said method comprising administering GLA or DGLA as such or in salt form other than the calcium salt or in other pharmacologically acceptable form convertible thereto in the body, optionally in association with EPA, DHA or other essential fatty acid of the n-3 or n-6 series additional to the GLA or DGLA as such or in salt or other pharmacologically acceptable form convertible thereto in the body.

3. A method according to claim 1 or 2 for treating or reducing the occurrence of calcium deficiency disease in patients at risk thereof.

4. A method according to claim 1 or 2 wherein said EPA, DHA or other essential fatty acid of the n-3 or n-6 series is administered as a calcium salt.

5. A method according to claim 1 or 2, wherein the amount of essential fatty acid administered is of from 0.01 to 1,000 mg/kg/day.

6. A method according to claim 5, wherein the amount of essential fatty acid administered is from 0.5 to 50 mg/kg/day.

7. A method according to claim 6, wherein the amount of essential fatty acid administered is from 2 to 30 mg/kg/day.

8. A method according to claim 5, wherein the fatty acids are administered in unit dosage form.

9. A method according to claim 3, wherein the calcium deficiency disease is osteoporosis.

10. A method for treating humans or animals having inadequate gut calcium absorption thereby increasing gut calcium absorption in humans or animals, said method comprising administering to said humans or animals gamma-linolenic acid (GLA) or dihomo-gamma-linolenic acid (DGLA) as such or in salt form other than the calcium salt or in other pharmacologically acceptable form convertible thereto in the body together with eicosapentaenoic acid (EPA), docosahexaenoic acid (DHA) or other essential fatty acid of the n-3 or n-6 series additional to the GLA or DGLA as a calcium salt or other pharmacologically acceptable form convertible thereto in the body.

11. A method for increasing the systemic calcium pool by stimulating both an increased absorption of and a reduction of urinary excretion of calcium in humans or animals suffering from low calcium absorption by administering GLA or DGLA to said humans or animals as such or in salt form other than the calcium salt or in other pharmacologically acceptable form convertible thereto in the body, optionally in association with EPA, DHA or other essential fatty acid of the n-3 or n-6 series additional to the GLA or DGLA as a calcium salt or other pharmacologically acceptable form convertible thereto in the body.

* * * * *